US010520399B2

(12) United States Patent
McInnes et al.

(10) Patent No.: US 10,520,399 B2
(45) Date of Patent: Dec. 31, 2019

(54) LIQUID SAMPLING

(71) Applicant: FLUID TRANSFER TECHNOLOGY PTY LTD, Welshpool, Western Australia (AU)

(72) Inventors: Luke William McInnes, Welshpool (AU); John Raymond Bondi, Welshpool (AU); Brian Mark Bondi, Welshpool (AU)

(73) Assignee: Fluid Transfer Technology Pty Ltd, Welshpool (AU)

( * ) Notice: Subject to any disclaimer, the term of this patent is extended or adjusted under 35 U.S.C. 154(b) by 160 days.

(21) Appl. No.: 15/549,669

(22) PCT Filed: Feb. 10, 2016

(86) PCT No.: PCT/AU2016/050077
§ 371 (c)(1),
(2) Date: Aug. 9, 2017

(87) PCT Pub. No.: WO2016/127211
PCT Pub. Date: Aug. 18, 2016

(65) Prior Publication Data
US 2018/0045616 A1    Feb. 15, 2018

(30) Foreign Application Priority Data

Feb. 10, 2015   (AU) ................................ 2015900421

(51) Int. Cl.
*G01N 1/14*    (2006.01)
*G01N 1/20*    (2006.01)

(52) U.S. Cl.
CPC ............. *G01N 1/14* (2013.01); *G01N 1/2035* (2013.01); *G01N 2001/1427* (2013.01); *G01N 2001/2071* (2013.01)

(58) Field of Classification Search
None
See application file for complete search history.

(56) References Cited

U.S. PATENT DOCUMENTS

| | | | | |
|---|---|---|---|---|
| 3,890,843 A | * | 6/1975 | Irwin ....................... | G01N 1/14 417/147 |
| 4,004,463 A | * | 1/1977 | Puthoff .................... | G01N 1/12 73/864.66 |
| 4,415,011 A | * | 11/1983 | Grant ....................... | B65B 3/30 141/284 |

(Continued)

FOREIGN PATENT DOCUMENTS

| | | |
|---|---|---|
| CN | 103808531 | 5/2014 |
| CN | 203847106 | 9/2014 |
| GB | 2262277 | 6/1993 |

*Primary Examiner* — Peter J Macchiarolo
*Assistant Examiner* — Mohammed E Keramet-Amircolai
(74) *Attorney, Agent, or Firm* — Winstead PC

(57) ABSTRACT

The invention provides a liquid sampler for the automated sampling of liquids at dedicated pre-determined intervals. The liquid sampler includes a liquid inlet connectable to a liquid circuit containing a liquid to be sampled, a sampling reservoir for collecting a liquid sample, and a sampling pump connected to the liquid inlet, operable to extract a discrete amount of liquid from the liquid inlet and to discharge the discrete amount of liquid into the sampling reservoir.

19 Claims, 1 Drawing Sheet

(56) References Cited

U.S. PATENT DOCUMENTS

| | | | | |
|---|---|---|---|---|
| 5,498,138 | A * | 3/1996 | Nimberger | F04B 9/107 417/401 |
| 6,422,737 | B1 * | 7/2002 | Welker | B01F 5/10 366/137 |
| 2002/0166392 | A1 * | 11/2002 | Handel | G01N 1/2035 73/863.83 |
| 2004/0123679 | A1 * | 7/2004 | Coleman | G01N 1/2247 73/863.72 |
| 2005/0002829 | A1 * | 1/2005 | Chen | G01N 1/14 422/503 |
| 2005/0006403 | A1 * | 1/2005 | Prineppi | F04B 43/1253 222/64 |
| 2009/0100902 | A1 * | 4/2009 | Miller | G01N 1/14 73/1.88 |
| 2010/0170350 | A1 * | 7/2010 | Stevens | G01N 1/14 73/864.34 |
| 2012/0115243 | A1 * | 5/2012 | Pitkanen | C12M 33/04 436/177 |
| 2017/0058670 | A1 * | 3/2017 | Hassell | B01F 5/0661 |
| 2017/0102308 | A1 * | 4/2017 | Gillette, II | G01N 11/00 |
| 2017/0233106 | A1 * | 8/2017 | Svanebjerg | B64F 5/23 244/134 C |

* cited by examiner

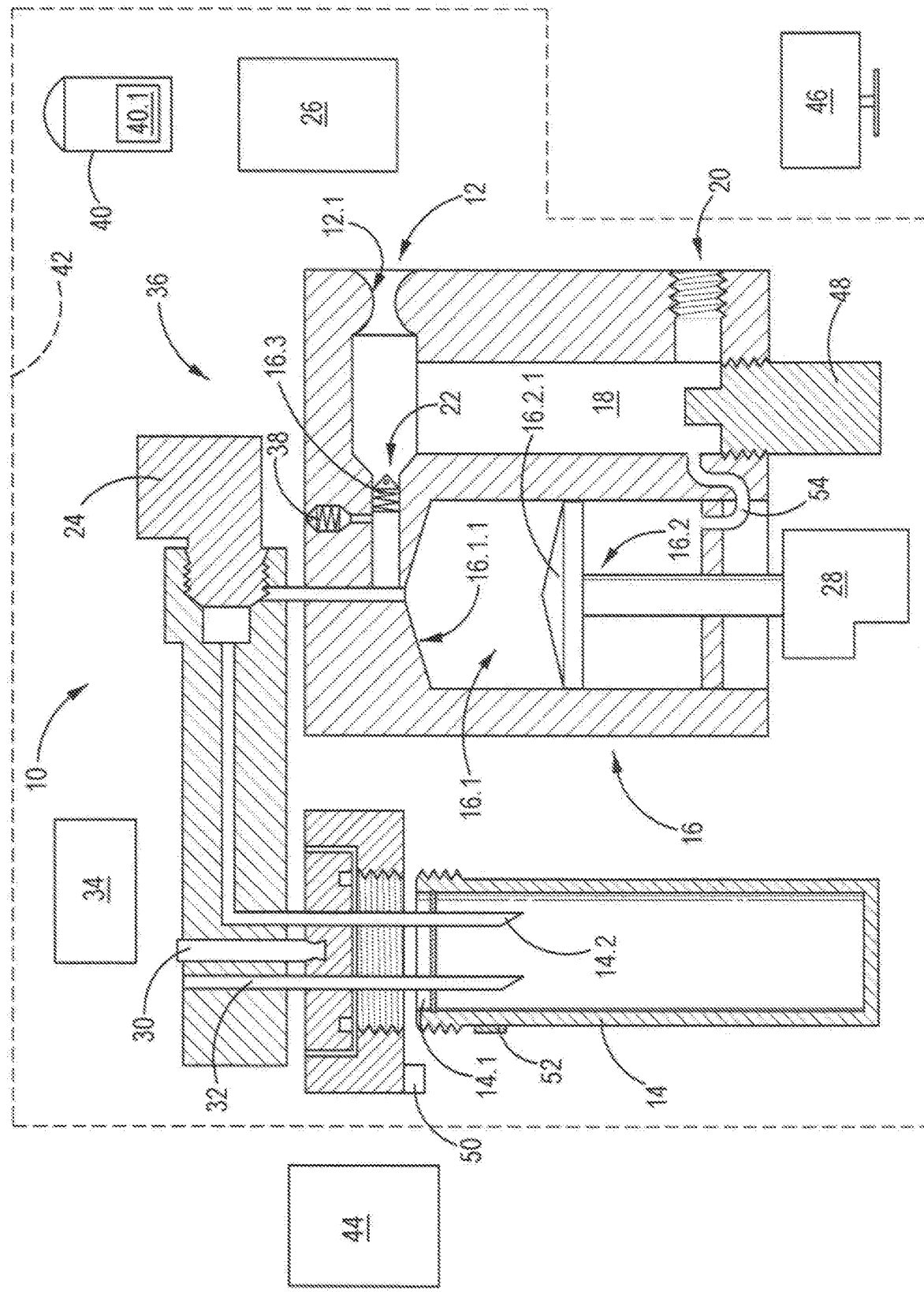

LIQUID SAMPLING

FIELD OF THE INVENTION

This invention relates to liquid sampling. In particular the invention relates to a liquid sampling device and to a method of sampling liquid.

BACKGROUND OF THE INVENTION

The inventor is aware of manual oil sampling methods that are employed to take oil samples from machinery for laboratory analysis. The results from the laboratory analysis are used to get an indication of the condition of the machinery. Defects in the maintenance or operation of the machinery can be identified by analyzing oil from such machinery. However sampling of live oil from machinery has become unreliable due to shortcomings in sampling procedures and strict Occupational Health and Safety requirements. Such sampling is error prone, given that significant amounts of time may pass between the time that the machinery needs to be sampled according to a sampling schedule, and the actual time that the machinery is sampled. This leads to errors that can be the result of inconsistent sampling, which in turn can result in severe damage to the equipment if underserviced, or unnecessary capital expenses if overserviced. It is an object of this invention to address at least some of these shortcomings.

SUMMARY OF THE INVENTION

According to one aspect of the invention, there is provided a liquid sampler, which includes:

a liquid inlet connectable to a liquid circuit containing a liquid to be sampled;

a sampling reservoir for collecting a liquid sample; and a sampling pump, the sampling pump connected to the liquid inlet, operable to extract a discrete amount of liquid from the liquid inlet and to discharge the discrete amount of liquid into the sampling reservoir.

The liquid inlet may include a flow control valve, such as a restriction valve, operable to control any one or both of the flow and pressure of the liquid from the liquid inlet to the sampling pump.

The liquid sampler may include a liquid flow chamber connected to the liquid inlet, the liquid flow chamber providing a constant volume of fresh liquid for extraction by the sampling pump. The liquid flow chamber may include an output port providing flow communication with the sampling pump. The liquid flow chamber may include a liquid outlet connectable to a liquid circuit containing the liquid to be sampled, for returning the excess fresh liquid to the liquid circuit.

The liquid sampler may include a liquid conditioning sensor in communication with a liquid to be sampled. The liquid conditioning sensor may be a di-electric sensor. The liquid sampler may also include a temperature sensor in communication with the liquid to be sampled.

In one embodiment, the sampling pump may include a reciprocally displaceable plunger disposed in a cylinder defining a sample chamber, the sampling pump having valves to control the flow into the sample chamber. In particular, the sampling pump may include a check valve between the liquid flow chamber and the sample chamber, operable to permit flow of liquid into the sample chamber but to prevent flow from the sample chamber back to the liquid flow chamber.

The sampling pump may be connected in flow communication with a second valve in a flow path between the sample chamber and the sampling reservoir. In one embodiment, the second valve may be in the form of a solenoid valve selectively controllable to permit liquid to flow from the sample chamber to the sample reservoir but to prevent liquid to flow in the reverse direction. In another embodiment, the second valve may be a check valve arranged to permit liquid flow from the sample chamber to the sample reservoir but to prevent liquid flow in the reverse direction.

The plunger may be displaceable between at least two positions, being a predefined measuring position in which the volume of the sample chamber is selectively predetermined and an extended position in which the volume of the sample chamber is at a minimum. The plunger may be displaceable into a third retracted position in which the volume of the sample chamber is a maximum. The plunger head may be conically shaped. An end of the sample cylinder may be shaped to accommodate the head of the plunger.

The sampling pump may include an actuator driving the plunger between the at least two positions. The actuator may be any one of an electric-, pneumatic-, or hydraulic actuator, or the like. The liquid sampler may include a controller controllably connected to the actuator and the solenoid valve. The controller may be operable to control the actuator in unison with the solenoid valve.

In use, the solenoid valve may be closed and the actuator may be controlled to move from the extended position to the measuring position to draw a liquid from the liquid flow chamber into the sample chamber through the check valve disposed between the two chambers.

The solenoid valve may then be opened and the actuator may be controlled to move from the measuring position to the extended position, thereby to transfer liquid from the sample chamber to the sampling reservoir.

The sample chamber may include a port located in an operatively side- or bottom wall thereof, such that excess oil that has weeped or seeped past the plunger may be drained back into the sample chamber.

The controller may be programmed to drive the actuator at predefined intervals, thereby to take liquid samples at predefined intervals. The sampling reservoir may be in the form of a removable container. The removable container may include sealing means. The sealing means may be in the form of a sheet material, which can be pierced. The liquid sampler may include a piercing tube operable to penetrate the sheet material.

In one embodiment, the sampling reservoir may have a threaded container mouth and the liquid sampler may include a threaded container receptacle matched to the threaded container mouth. In another embodiment, the sampling reservoir may have a bayonet formation proximate its mouth and the liquid sampler may include a bayonet receptacle matched to the bayonet formation proximate the container mouth.

The liquid sampler may include a container sensor operable to sense when a removable container is received into the threaded receptacle. The controller may be programmed to inhibit taking liquid samples when the container sensor does not sense a container in the receptacle. Furthermore, the liquid sampler may include a near-field reader, typically in the form of a radio-frequency reader ("RFI") reader, which can interrogate or read a unique tag, typically an RFID tag, associated with the sampling tube. This may assist in generating and keeping an audit trail of each sampling tube for each piece of equipment which the liquid sampler of the invention is to be applied to, as well as minimising errors.

The liquid sampler may include a piercing ventilation tube receivable into the container through the sheet material through which excess liquid can be expelled. The liquid sampler may include an overflow container in flow communication with the ventilation tube, in use to collect excess liquid expelled from the ventilation tube. The liquid sampler may include a purge circuit. The purge circuit may have a purge inlet valve located proximate the output port of the liquid flow chamber. The purge inlet valve may be a check valve operable to permit a purge fluid to pass through the purge inlet valve but to block fluid flow in the reverse direction.

The purge circuit may include a pressurized purge fluid source connectable in flow communication with the purge inlet valve. The purge circuit may include a purge solenoid valve disposed in the fluid flow circuit between the pressurized purge fluid source and the purge inlet valve, operable to control flow of the purge fluid through the purge inlet valve. The purge solenoid valve may be controllably connected to the controller, operable to work in unison with the actuator and the second solenoid valve. The controller may be programmed to open the purge solenoid valve after a sample has been discharged into the sampling reservoir. The liquid sampler may include a hermetically sealed enclosure into which its components are mounted. The sealed enclosure may include pressurization means, operable to pressurize the inside of the enclosure to maintain a positive pressure inside the enclosure, thereby to minimize the risk of sample contamination.

The invention extends to a method of sampling liquid, the method including the steps of:
  installing a liquid sampler, as described onto equipment from which a liquid is to be sampled;
  programming the controller of the liquid sampler with a sampling regime; and
  collecting a liquid sample taken in accordance with the sampling regime in the sampling reservoir.

The sampling regime may be a predefined sampling time interval. This may, in certain applications, be every 250 hours, or any prescribed regimen interval that needs to be adhered to, to ensure consistent sampling and reporting results.

In a preferred embodiment, the liquid to be sampled may be oil and the equipment from which the liquid is to be sampled may be a motorized vehicle. Alternatively, the equipment from which the liquid is to be sampled may be an aircraft, marine vessel, or a fixed plant.

Further features of the present invention are more fully described in the following description of several non-limiting embodiments included solely for the purposes of exemplifying the present invention. The following description is not a restriction on the broad summary, disclosure or description of the invention as set out above and is made with reference to the accompanying drawing.

DRAWING(S)

In the drawing(s):
FIG. 1 shows a schematic block diagram of a liquid sampler in accordance with the invention.

DESCRIPTION OF EMBODIMENTS

A schematic block diagram of a liquid sampler 10 in accordance with one aspect of the invention is shown in FIG. 1. As used herein the term "liquid" may also include fluid or gas. This particular example is for an oil sampler and all references to liquid should thus be understood to refer to oil. The liquid sampler 10 according to one aspect of the invention has a liquid inlet 12 connectable to a liquid circuit of a vehicle (not shown) containing a liquid to be sampled. The liquid sampler 10 further has a sampling reservoir 14 for collecting a liquid sample and a sampling pump 16 connected to the liquid inlet, operable to extract a discrete amount of liquid from the liquid inlet 12 and to discharge the discrete amount of liquid into the sampling reservoir 16. The amount of fluid is typically a measurable amount of fluid and is prescribed by or dictated by operating conditions or manufacturer's recommendations. The sampling reservoir 14 is in the form of a tube or vial and is hermetically sealed prior to use to prevent debris from entering prior to attachment of the sampling reservoir 14 to the liquid sampler 10. The liquid inlet 12 has a restriction valve 12.1, arranged to control the flow and pressure of the liquid from the liquid inlet 12 to the sampling pump 16.

A liquid flow chamber 18 is provided between the liquid inlet 12 and the sampling pump 16 to provide a constant volume of fresh liquid for extraction by the sampling pump 16. The liquid flow chamber 18 further has a liquid outlet 20 connectable to the liquid circuit to provide a liquid return path to the liquid circuit. Liquid is circulated from the liquid inlet 12 to the liquid outlet 20 through the liquid flow chamber 18. The liquid sampler 10 has a liquid conditioning sensor 48 disposed at the bottom of the liquid flow chamber 18 and in communication with the liquid in the liquid flow chamber 18. Typically the liquid conditioning sensor 48 is a di-electric sensor. The liquid sampler 10 can optionally also include a temperature sensor (not shown) in communication with the liquid to be sampled. The liquid flow chamber 18 has an output port 22 providing fluid flow communication with the sampling pump 16.

The sampling pump 16 has a cylinder 16.1 in which a plunger 16.2 is reciprocally displaceable. The pump 16 includes an inlet check valve 16.3 in the output port 22 from the liquid flow chamber. The check valve 16.3 is arranged only to permit liquid flow from the flow chamber 18 to the cylinder 16.1 of the sampling pump 16. The sampling pump 16 is connected in fluid flow communication with a second valve 24, being a solenoid valve, interposed in a flow path between the sample chamber 16.1 and the sampling reservoir 14. The second (solenoid) valve 24 is selectively controllable to permit liquid to flow from the sample chamber 16.1 to the sample reservoir 14 but to prevent liquid to flow in the reverse direction. The solenoid valve 24 is controllable from a controller 26, discussed in more detail below.

The plunger 16.2 is displaceable between three positions, being a predefined measuring position in which the volume of the sample chamber is selectively predetermined, an extended position in which the volume of the sample chamber is at a minimum, and a retracted position in which the volume of the sample chamber is at a maximum. The plunger 16.2 has a head 16.2.1, which is conically shaped. An end 16.1.1 of the sample cylinder 16.1 is complementarily shaped to accommodate the head 16.2.1 of the plunger 16.2, thereby to ensure that the head 16.2.1 can seal off against the end 16.1.1 of the sample cylinder 16.1.

The sampling pump 16 has an actuator 28 connected to the plunger 16.2 for driving the plunger 16.2 between the three positions. The actuator 28 can be any one of an electric-, pneumatic-, or hydraulic actuator, depending on the suitability to the rest of the installation (not shown).

The controller 26 is controllably connected to the actuator 28 and the solenoid valve 24. The controller is operable to control the actuator 28 in unison with the solenoid valve 24. The controller's 26 control sequence will be to close the solenoid valve 24 and to activate the actuator 28 to move from the extended position to the measuring position to draw a liquid from the liquid flow chamber 18 to the sample chamber 16.1 through the check valve 22 disposed between the two chambers. The solenoid valve 24 is then opened and the actuator 28 is activated to move from the measuring position to the extended position, thereby to transfer liquid from the sample chamber 16.1 to the sampling reservoir 14. The controller in this example is programmed to drive the actuator at predefined intervals, thereby to take liquid samples at predefined intervals, such as every 250 hours.

The liquid within the sample chamber 16.1 also serves to lubricate the skirt of the plunger 16.2.1. As such, some liquid build-up or seepage may occasionally occur below the plunger 16.2, the liquid then being drained back to the liquid flow chamber 18 via port 54 located within the base of the sample chamber 16.1. It follows that the port 54 can also be located within a lower part sidewall of the sample chamber 16.1, below the lower edge of the plunger 16.2 when fully retracted.

The sampling reservoir 14 is a removable container. The removable container 14 has a film seal 14.1 extending over and closing the mouth thereof. The film seal 14.1 can be pierced by a piercing tube 14.2. As can be seen the container 14 has a threaded mouth and the liquid sampler 10 has a threaded container receptacle matched to the threaded container mouth.

The liquid sampler 10 includes a container sensor 30 operable to sense when a removable container 14 is received into the threaded receptacle. The controller is programmed to inhibit the taking of liquid samples when the container sensor does not sense a container in the receptacle. It may also generate a warning signal to an operator via telemetry or other signaling means (not shown).

Furthermore, the liquid sampler 10 includes a near-field reader in the form of an RFID reader 50 which can interrogate or read an RFID tag 52 associated with the sampling reservoir 52, in this way ensuring that allocation errors are minimised and to generate an audit trail of each removable container/sampling reservoir 14.

In addition, the liquid sampler 10 has a piercing ventilation tube 32 receivable into the container 14 through the film seal 14.1 through which excess liquid can be expelled. The liquid sampler 10 includes an overflow container 34 in fluid flow communication with the ventilation tube 32 whereby, in use, excess liquid expelled from the ventilation tube 32 can be collected.

The liquid sampler 10 further includes a purge circuit 36. The purge circuit 36 has a purge inlet valve 38 located proximate the output port 22 of the liquid flow chamber 18. The purge inlet valve 38 is a check valve operable not only to permit a purge fluid to pass through the purge inlet valve 38 towards the sample chamber 16.1, but to also block fluid flow in the reverse direction.

The purge circuit 36 includes a pressurized purge fluid source in the form of a pressurized gas canister 40 connectable in flow communication with the purge inlet valve 38. The purge circuit 38 includes a purge solenoid valve 40.1 disposed in the fluid flow circuit between the gas canister 40 and the purge inlet valve 38, operable to control flow of the purge fluid through the purge inlet valve 38. The purge solenoid valve 40.1 is controllably connected to the controller 26, operable to work in unison with the actuator 28 and the second solenoid valve 24. The controller 26 is programmed to open the purge solenoid valve 40.1 after a sample has been discharged into the sampling reservoir 14.

The liquid sampler 10 includes a hermetically sealed enclosure 42 (shown in broken line) into which its components are mounted. The sealed enclosure 42 has a pressure pump 44, operable to pressurize the inside of the enclosure 42 to maintain a positive pressure inside the enclosure 42, thereby to minimize the risk of sample contamination.

The controller 26 can be brought in communication with a monitoring station 46 to which data can be downloaded. The controller can also include telemetry that can feed information into a vehicle conditioning and positioning/tracking system, as required. The Applicant is of the opinion that the liquid sampler 10 disclosed in the specification will overcome at least some of the shortcomings of taking consistent, reliable liquid samples at dedicated time intervals from equipment.

Optional embodiments of the present invention may also be said to broadly consist in the parts, elements and features referred to or indicated herein, individually or collectively, in any or all combinations of two or more of the parts, elements or features, and wherein specific integers are mentioned herein which have known equivalents in the art to which the invention relates, such known equivalents are deemed to be incorporated herein as if individually set forth. It is to be appreciated that reference to "one example" or "an example" of the invention is not made in an exclusive sense. Accordingly, one example may exemplify certain aspects of the invention, whilst other aspects are exemplified in a different example. These examples are intended to assist the skilled person in performing the invention and are not intended to limit the overall scope of the invention in any way unless the context clearly indicates otherwise. It is to be understood that the terminology employed above is for the purpose of description and should not be regarded as limiting. The described embodiment is intended to be illustrative of the invention, without limiting the scope thereof. The invention is capable of being practised with various modifications and additions as will readily occur to those skilled in the art. Various substantially and specifically practical and useful exemplary embodiments of the claimed subject matter are described herein, textually and/or graphically, including the best mode, if any, known to the inventors for carrying out the claimed subject matter. Variations (e.g. modifications and/or enhancements) of one or more embodiments described herein might become apparent to those of ordinary skill in the art upon reading this application. The inventor(s) expects skilled artisans to employ such variations as appropriate, and the inventor(s) intends for the claimed subject matter to be practiced other than as specifically described herein. Accordingly, as permitted by law, the claimed subject matter includes and covers all equivalents of the claimed subject matter and all improvements to the claimed subject matter. Moreover, every combination of the above described elements, activities, and all possible variations thereof are encompassed by the claimed subject matter unless otherwise clearly indicated herein, clearly and specifically disclaimed, or otherwise clearly contradicted by context.

The use of any and all examples, or exemplary language (e.g., "such as") provided herein, is intended merely to better illuminate one or more embodiments and does not pose a limitation on the scope of any claimed subject matter unless otherwise stated. No language in the specification should be construed as indicating any non-claimed subject matter as essential to the practice of the claimed subject matter. The use of words that indicate orientation or direction of travel is not to be considered limiting. Thus, words such as "front", "back", "rear", "side", "up", "down", "upper", "lower", "top", "bottom", "forwards", "backwards", "towards", "distal", "proximal", "in", "out" and synonyms, antonyms and derivatives thereof have been selected for convenience only, unless the context indicates otherwise. The inventor(s) envisage that various exemplary embodiments of the claimed subject matter can be supplied in any particular orientation and the claimed subject matter is intended to include such orientations. The use of the terms "a", "an", "said", "the", and/or similar referents in the context of describing various embodiments (especially in the context of the claimed subject matter) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Moreover, when any number or range is described herein, unless clearly stated otherwise, that number or range is approximate. Recitation of ranges of values herein are merely intended to serve as a shorthand method of referring individually to each separate value falling within the range, unless otherwise indicated herein, and each separate value and each separate sub-range defined by such separate values is incorporated into the specification as if it were individually recited herein. For example, if a range of 1 to 10 is described, that range includes all values there between, such as for example, 1.1, 2.5, 3.335, 5, 6.179, 8.9999, etc., and includes all sub-ranges there between, such as for example, 1 to 3.65, 2.8 to 8.14, 1.93 to 9, etc.

Accordingly, every portion (e.g., title, field, background, summary, description, abstract, drawing FIGURE, etc.) of this application, other than the claims themselves, is to be regarded as illustrative in nature, and not as restrictive; and the scope of subject matter protected by any patent that issues based on this application is defined only by the claims of that patent.

The invention claimed is:

1. A liquid sampler, comprising:
a liquid inlet connectable to a liquid circuit containing a liquid to be sampled;
a sampling reservoir for collecting a liquid sample, wherein the sampling reservoir comprises a removable container;
a sampling pump connected to the liquid inlet and operable to extract a discrete amount of liquid from the liquid inlet and to discharge the discrete amount of liquid into the sampling reservoir, the sampling pump having a reciprocally displaceable plunger disposed in a sample chamber shaped to accommodate a head of the plunger, the plunger displaceable between at least two positions, being a predefined measuring position in which the volume of the sample chamber is selectively predetermined and an extended position in which the volume of the sample chamber is at a minimum, the sampling pump having an actuator driving the plunger between the at least two positions; and
a controller controllably connected to the actuator, the controller programmed to drive the actuator at predefined intervals in order to take liquid samples at predefined intervals;
wherein the liquid sampler includes a hermetically sealed enclosure into which its components are mounted, said hermetically sealed enclosure including pressurization means operable to pressurize the inside of the hermetically sealed enclosure to maintain a positive pressure inside the hermetically sealed enclosure, thereby to minimize a risk of sample contamination; and
wherein the liquid sampler includes a container sensor operable to sense when a removable container is appropriately received inside the sealed enclosure, the controller programmed to inhibit taking liquid samples when the container sensor does not sense a container in the enclosure.

2. The liquid sampler of claim 1, wherein liquid inlet includes a flow control valve, such as a restriction valve, operable to control any one or both of the flow and pressure of the liquid from the liquid inlet to the sampling pump.

3. The liquid sampler of claim 2, further comprising a liquid flow chamber connected to the liquid inlet, the liquid flow chamber providing a constant volume of fresh liquid for extraction by the sampling pump, and the liquid flow chamber including an output port providing flow communication with the sampling pump.

4. The liquid sampler of claim 3, wherein the liquid flow chamber includes a liquid outlet connectable to a liquid circuit containing the liquid to be sampled, for returning excess fresh liquid to the liquid circuit.

5. The liquid sampler of claim 3, wherein the sampling pump includes valves to control the flow into the sample chamber, and the sampling pump including a check valve between the liquid flow chamber and the sample chamber, operable to permit flow of liquid into the sample chamber but to prevent flow from the sample chamber back to the liquid flow chamber.

6. The liquid sampler of claim 3, further comprising a purge circuit having a purge inlet valve located proximate the output port of the liquid flow chamber, wherein the purge inlet valve is a check valve operable to permit a purge fluid to pass through the purge inlet valve, but to block fluid flow in the reverse direction, and the purge circuit including a pressurized purge fluid source connectable in flow communication with the purge inlet valve.

7. The liquid sampler of claim 6, wherein the purge circuit includes a purge solenoid valve disposed in a fluid flow circuit between the pressurized purge fluid source and the purge inlet valve, operable to control flow of the purge fluid through the purge inlet valve, the purge solenoid valve controllably connected to the controller, operable to work in unison with the actuator and the second valve, and the controller programmed to open the purge solenoid valve after a sample has been discharged into the sampling reservoir.

8. The liquid sampler of claim 1, further comprising a liquid conditioning sensor in communication with a liquid to be sampled.

9. The liquid sampler of claim 1, further comprising a temperature sensor in communication with the liquid to be sampled.

10. The liquid sampler of claim 1, wherein the sampling pump is connected in flow communication with a second valve in a flow path between the sample chamber and the sampling reservoir, and the second valve, being a solenoid or check valve, is configured to permit liquid to flow from the sample chamber to the sample reservoir but to prevent liquid to flow in the reverse direction.

11. The liquid sampler of claim 1, wherein the plunger is displaceable into a third, retracted position in which the volume of the sample chamber is a maximum.

12. The liquid sampler of claim 10, wherein the controller is controllably connected to the second valve and is operable to control the actuator in unison with the second valve.

13. The liquid sampler of claim 10, wherein, in use, the second valve is closed and the actuator is controlled to move from the extended position to the measuring position to draw a liquid from the liquid flow chamber into the sample chamber through the check valve disposed between the two chambers, whereafter the second valve is opened and the actuator is controlled to move from the measuring position to the extended position, thereby to transfer liquid from the sample chamber to the sampling reservoir.

14. The liquid sampler of claim 1, wherein:
the sampling reservoir is in the form of a removable container that includes a sealing means in the form of a pierceable sheet material; and
the liquid sampler comprises a piercing tube operable to penetrate the pierceable sheet material.

15. The liquid sampler of claim 14, further comprising:
a piercing ventilation tube receivable into the sampling reservoir through the pierceable sheet material and through which excess liquid can be expelled; and
an overflow container in flow communication with the ventilation tube and configured to collect excess liquid expelled from the ventilation tube.

16. The liquid sampler of claim 1, wherein the sampling reservoir has a threaded container mouth and the liquid sampler includes a threaded container receptacle matched to the threaded container mouth.

17. The liquid sampler of claim 16, further comprising:
a container sensor operable to sense when the removable container is received into the threaded container receptacle; and
wherein the controller is programmed to inhibit taking liquid samples when the removable container sensor is not secured to the liquid sampler.

18. The liquid sampler of claim 1, wherein the sampling reservoir has a bayonet formation proximate a mouth of the sampling reservoir and the liquid sampler includes a bayonet receptacle matched to the bayonet formation, proximate the mouth of the sampling reservoir.

19. The liquid sampler of claim 1, further comprising a near-field reader in the form of an RFID reader that can interrogate or read an RFID tag associated with the sampling reservoir.

* * * * *